(12) United States Patent
Buehler et al.

(10) Patent No.: US 11,213,537 B2
(45) Date of Patent: Jan. 4, 2022

(54) INHIBITION OF AUTISM SPECTRUM DISORDER USING RIBOSOMAL READ-THROUGH COMPOUNDS

(71) Applicant: Friedrich Miescher Institute for Biomedical Research, Basel (CH)

(72) Inventors: Marc Buehler, Riehen (CH); Veronica Ostapcuk, Krupka (CZ)

(73) Assignee: FRIEDRICH MIESCHER INSTITUTE FOR BIOMEDICAL RESEARCH, Basel (CH)

( * ) Notice: Subject to any disclaimer, the term of this patent is extended or adjusted under 35 U.S.C. 154(b) by 0 days.

(21) Appl. No.: 16/647,591

(22) PCT Filed: Sep. 17, 2018

(86) PCT No.: PCT/IB2018/057095
§ 371 (c)(1),
(2) Date: Mar. 16, 2020

(87) PCT Pub. No.: WO2019/053667
PCT Pub. Date: Mar. 21, 2019

(65) Prior Publication Data
US 2020/0261484 A1    Aug. 20, 2020

(30) Foreign Application Priority Data
Sep. 18, 2017    (EP) .................................... 17191642

(51) Int. Cl.
| *A61K 31/7036* | (2006.01) |
| *A61K 31/165* | (2006.01) |
| *A61K 31/4245* | (2006.01) |
| *A61K 31/5377* | (2006.01) |
| *A61K 31/7048* | (2006.01) |

(52) U.S. Cl.
CPC ........ *A61K 31/7036* (2013.01); *A61K 31/165* (2013.01); *A61K 31/4245* (2013.01); *A61K 31/5377* (2013.01); *A61K 31/7048* (2013.01)

(58) Field of Classification Search
CPC .............. A61K 31/7036; A61K 31/165; A61K 31/7048; A61K 31/5377; A61K 31/4245
USPC ........................................................ 514/39
See application file for complete search history.

(56) References Cited

U.S. PATENT DOCUMENTS

| 5,840,702 A | 11/1998 | Bedwell et al. |
| 2004/0072201 A1 | 4/2004 | Dietz et al. |
| 2005/0261210 A1* | 11/2005 | Bhatnagar ............ A61K 31/704 514/35 |
| 2015/0328247 A1 | 11/2015 | Rosin-Arbesfeld et al. |
| 2016/0089363 A1 | 3/2016 | Borody et al. |
| 2016/0194630 A1* | 7/2016 | Krainer ............... A61K 31/7105 514/44 A |

OTHER PUBLICATIONS

Sifrim et al. Distinct genetic architectures for syndromic and nonsyndromic congenital heart defects identified by exome sequencing. Nature Genetics 48(9):1060-1064, 2016. (Year: 2016).*
Du et al., "Aminoglycoside suppression of a premature stop mutation in a Ctfr-/- mouse carrying a human CFTR-G542X transgene," J Mol Med (Berl), 80(9), 595-604 (2002) (abstract).
Gomez-Grau, et al., "Evaluation of Aminoglycoside and Non-Aminoglycoside Compounds for Stop-Codon Readthrough Therapy in Four Lysosomal Storage Diseases," PLoS ONE 10(8):1-18 (2015).
Gozes, et al., "The Eight and a Half Year Journey of Undiagnosed AD: Gene Sequencing and Funding of Advanced Genetic Testing Has Led to Hope and New Beginnings," Frontiers in Endocrinology, 8(107): 1-14 (2017).
Helip-Wooley et al., "Expression of CTNS alleles: subcellular localization and aminoglycoside correction in vitro," Mol Genet Metab, 75(2), 128-33. (2002) (abstract).
Helsmoortel, et al., "A SWI/SNF-related autism syndrome caused by de novo mutations in ADNP," Nature Genetics, 46(4):380-384, (2014).
Keeling et al., "Gentamicin-mediated suppression of Hurler syndrome stop mutations restores a low level of alpha-L-iduronidase activity and reduces lysosomal glycosaminoglycan accumulation," Hum Mol Genet, 10(3), 291-9 (2001).
Krajewska-Walasek, et al., "Additional data on the clinical phenotype of Helsmoortel-Van der Aa syndrome associated with a novel truncating mutation in ADNP gene," American Journal of Medical Genetics 170(6):1647-1650 (2016).
Lai et al., "Correction of ATM gene function by aminoglycoside-induced read-through of premature termination codons," Proc Natl Acad Sci USA, 101(44), 15676-81 (2004).
Loufrani et al., "Absence of dystrophin in mice reduces NO-dependent vascular function and vascular density: total recovery after a treatment with the aminoglycoside gentamicin," Arterioscler Thromb Vasc Biol, 24(4), 671-6(2004).
Peltz, et al., "Ataluren as an agent for therapeutic nonsense suppression," Annu Rev Med. 64:407-425, (2013).
Rebibo-Sabbah, et al., "In vitro and ex vivo suppression by aminoglycosides of PCDH15 nonsense mutations underlying type 1 Usher syndrome," Hum Genet, 122(3-4), 373-81 (2007) (abstract).
Sossi et al., "Premature termination mutations in exon 3 of the SMN1 gene are associated with exon skipping and a relatively mild SMA phenotype," Eur J Hum Genet, 9(2):113-20 (2001).
Thompson, et al., "Effects of a number of classes of 50S inhibitors on stop codon readthrough during protein synthesis," Antimicrobial Agents and Chemotherapy, 48(12):4889-4891 (2004).
Zingman, et al., "Aminoglycoside-induced translational read-through in disease: overcoming nonsense mutations by pharmacogenetic therapy," Clinical Pharmacology Therapeutics, 81(1), 99-103. (2007) (abstract).

* cited by examiner

*Primary Examiner* — Yih-Horng Shiao
(74) *Attorney, Agent, or Firm* — Hoxie & Associates LLC

(57) ABSTRACT

The present invention relates to the novel use of read-through compounds for use in the treatment and/or prevention of Autism Spectrum Disorder.

9 Claims, 5 Drawing Sheets

|  | Adnp^PTC718 | Chd4 | HP1β | HP1γ |  |
|---|---|---|---|---|---|
|  | 290 / 20 / 19% | 13 / 8 / 4% | -/-/- | -/-/- | untreated |
|  | 520 / 35 / 39% | 84 / 29 / 14% | 27 / 7 / 45% | 49 / 6 / 38% | gentamycin |
|  | 417 / 33 / 31% | 40 / 21 / 10% | -/-/- | 5 / 3 / 22% | paromomycin | total spectrum count / total unique peptide count / % sequence coverage

Figure 4

INHIBITION OF AUTISM SPECTRUM DISORDER USING RIBOSOMAL READ-THROUGH COMPOUNDS

TECHNICAL FIELD

The present disclosure relates to a novel use of ribosomal read-through compounds for the prevention and/or treatment of Autism Spectrum Disorder (ASD).

BACKGROUND OF THE INVENTION

Autism Spectrum disorders (ASD) are a heterogeneous group of serious neurodevelopmental disorders that manifest during early childhood and are characterized by stereotyped interests and impairments in social interaction and communication. The term "spectrum" refers to the wide range of symptoms, skills, and levels of impairment, or disability, that patients with ASD can have. ASD is generally diagnosed according to current guidelines. The guidelines currently defines five disorders, sometimes called pervasive developmental disorders (PDDs), as ASD, including Autistic disorder (classic autism), Asperger's disorder (Asperger syndrome), Pervasive developmental disorder not otherwise specified (PDD-NOS), Rett's disorder (Rett syndrome), and Childhood disintegrative disorder (CDD). Some patients are mildly impaired by their symptoms, but others are severely disabled. ASD encompasses a set of complex disorders with poorly defined etiologies, and no targeted cure.

The reported incidence of autism has rapidly increased to 1 in 88 births in the United States as of 2008 (CDC, 2012), and the diagnosis has increased 10-fold over the past four decades, representing a significant medical and social burden in the coming decades. There is growing support for contributions by both genetic and environmental risk factors in ASD, yet little is known about the etiology and underlying neuropathology, and there are no clear biological markers for these disorders. The striking heterogeneity among individuals that share the same diagnosis is consistent with the prevailing notion that there are a variety of etiologies for ASD.

The genetic basis of autism has been extensively studied in the past decade using three complementary approaches: cytogenetic studies, linkage analysis, and candidate gene analysis. Searches for chromosomal abnormalities in autism have revealed terminal and interstitial deletions, balanced and unbalanced translocations, and inversions on a large number of chromosomes, with abnormalities on chromosomes 15, 7, and X being reported most frequently. Other evidence for a genetic basis of autistic endophenotypes comes from the study of disorders that share phenotypic features that overlap with autism such as Fragile X syndrome and Rett syndrome.

SUMMARY OF THE INVENTION

The present inventors serendipitously found the novel repressive protein complex consisting of Chd4, Adnp, and HP1beta/gamma. This complex prevents premature expression of lineage specifying genes in mouse embryonic stem cells (mES) cells independent of H3K9me3 modified nucleosomes. Adnp is a key subunit of this complex, and is crucial for complex assembly and its targeting to specific euchromatic sites in the genome. These findings offer an explanation for why several organs and functions of the body are affected in ASD patients with mutations in ADNP, where most known mutations are frameshift or nonsense mutations that result in C-terminal truncations of Adnp, including the homeobox domain and the HP1 interaction motif. The inability of ADNP to bind lineage-specifying genes or interact with HP1 proteins can cause Adnp-linked diseases. Therefore, patients with nonsense mutations in ADNP will benefit from therapeutic agents that are being developed to promote ribosomal read-through of premature stop codons.

The present invention thus provides the novel use of compounds promoting ribosomal read-through of premature stop codons in the prevention and/or treatment of Autism Spectrum Disorder (ASD).

The preferred therapeutic and/or prophylactic methods of the invention in general comprise administration of a therapeutically effective amount of a pharmaceutical composition comprising a compound that induces read-through of premature termination codons (PTCs) to an animal in need thereof, including a mammal, particularly a human. Also provided is a therapeutically effective amount of a pharmaceutical composition comprising a compound that induces read-through of PTCs and an effective amount of a compound that inhibits nonstop mediated mRNA decay pathways (NSD) to an animal in need thereof, including a mammal, particularly a human. The compounds may be provided in the same pharmaceutical composition, or as separate compositions. Such treatment will be suitably administered to subjects, particularly humans, suffering from, having, susceptible to, or at risk for a genetic disorder.

BRIEF DESCRIPTION OF THE DRAWINGS

FIG. 4 Compounds promoting stop codon read-through restore the formation of the ChAHP complex. FLAG/Avi-tagged Adnp-PTC718 was streptavidin purified from cells with and without aminoglycoside treatment and subjected to LC-MS/MS analysis. Adnp-PTC718 expressing cells were treated with 2 mg/ml gentamycin (2.9 mM) or paromomycin (3.2 mM) for 24 hours. The table depicts total spectral counts, unique peptides and percent sequence coverage for all ChAHP components from the different treatments.

DETAILED DESCRIPTION OF THE INVENTION

Figure 1:
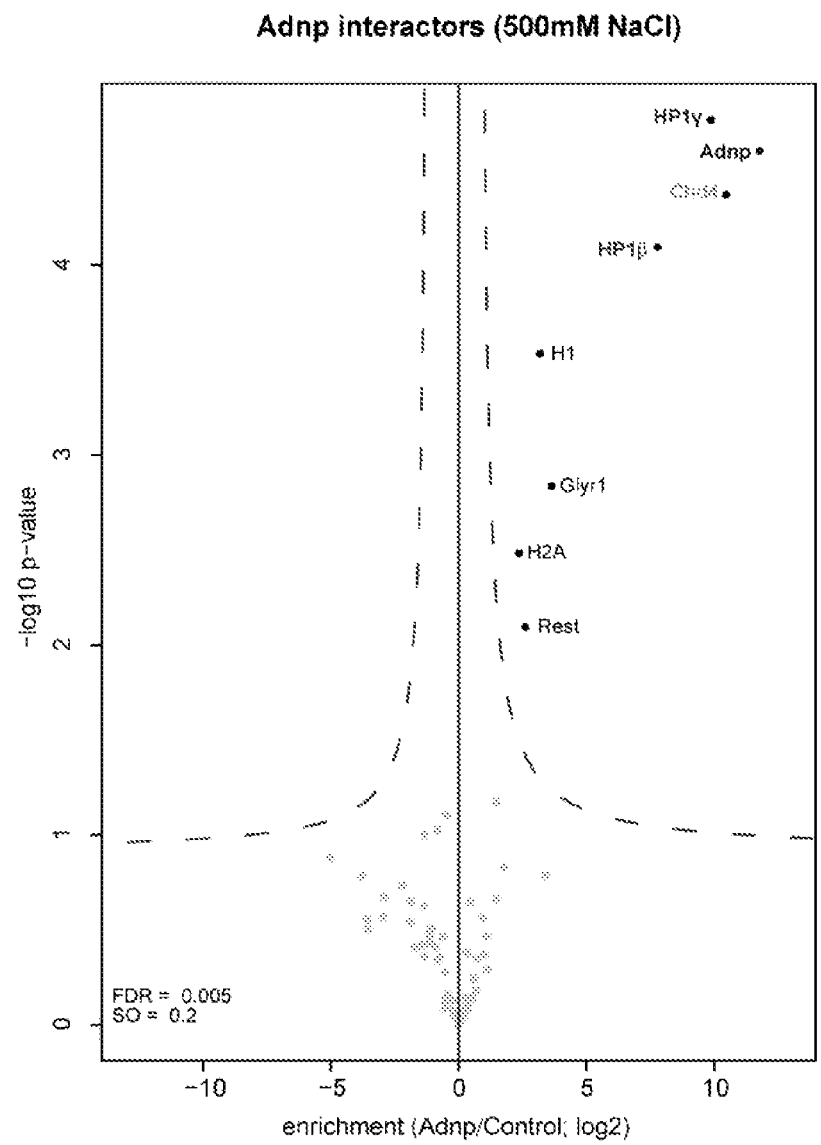
FIG. 1 Adnp mediates ChAHP complex formation (1) TAP-LC-MS/MS of endogenously FLAG/Avi-tagged Adnp. Protein purification was performed in the presence of 500 mM NaCl. Parental mES cell line serves as background control. n=3 independent biological replicates (i.e. 3 independent Adnp$^{FlagAvi/FlagAvi}$ mES cell lines). Statistical analysis was done with Perseus (see methods for details). Mass spectrometry raw data is deposited with ProteomeXchange.
Figure 2:
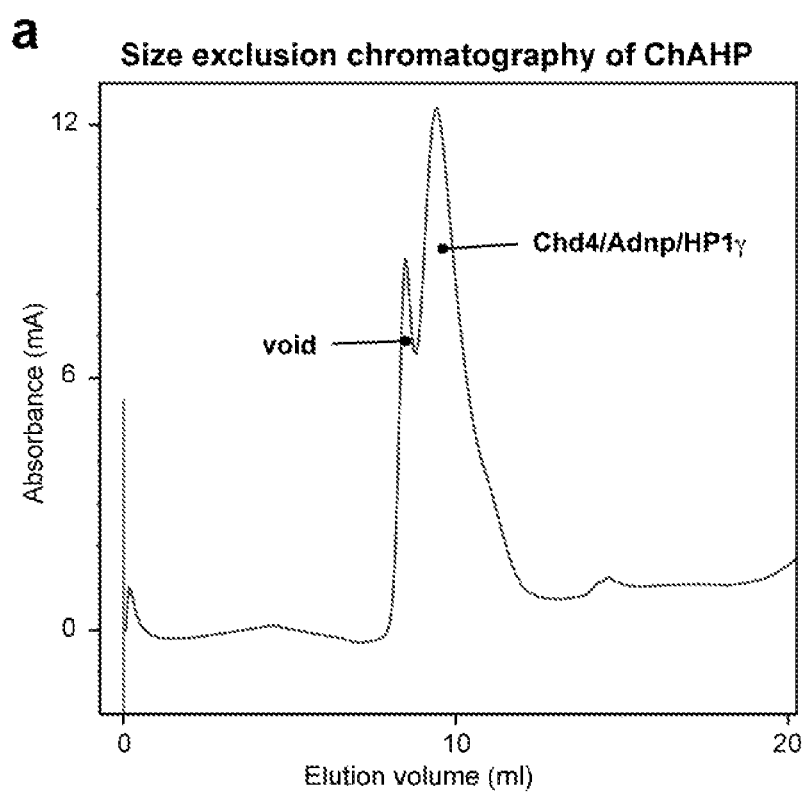
FIG. 2 Adnp mediates ChAHP complex formation (2) First Panel: In vitro reconstitution of the ChAHP complex. ADNP, CHD4, and HP1gamma were expressed in Hi5 insect cells. Strep-HP1gamma was pulled down with co-purifying ADNP and CHD4, followed by separation on size exclusion chromatography (SEC). Fraction containing purified ChAHP was loaded on SDS-PAGE and reinjected on SEC. Second Panel: Strep pulldown assays with proteins overexpressed in Hi5 insect cells. ADNP directly interacts with CHD4 or HP1gamma. CHD4 and HP1gamma do not interact in the absence of ADNP. Third Panel: Scheme depicting ChAHP subunit interactions. Adnp N-terminal zinc fingers are necessary for the interaction with Chd4. P*V*L motif in Adnp mediates the interaction with the chromo shadow domain (CSD) of HP1. Protein domains as predicted by InterPro.
Figure 2:
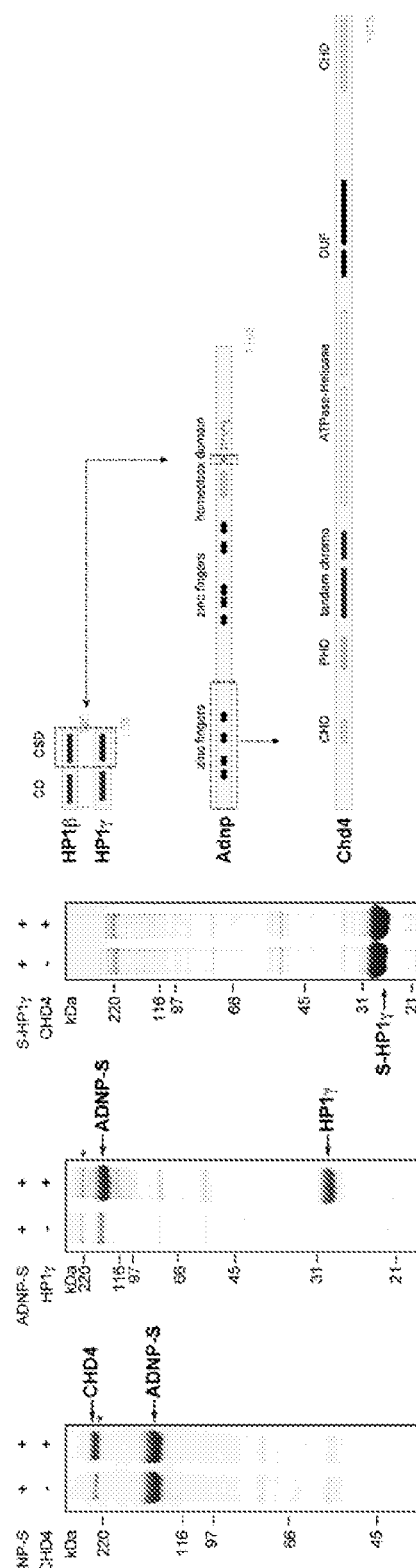
Figure 3:
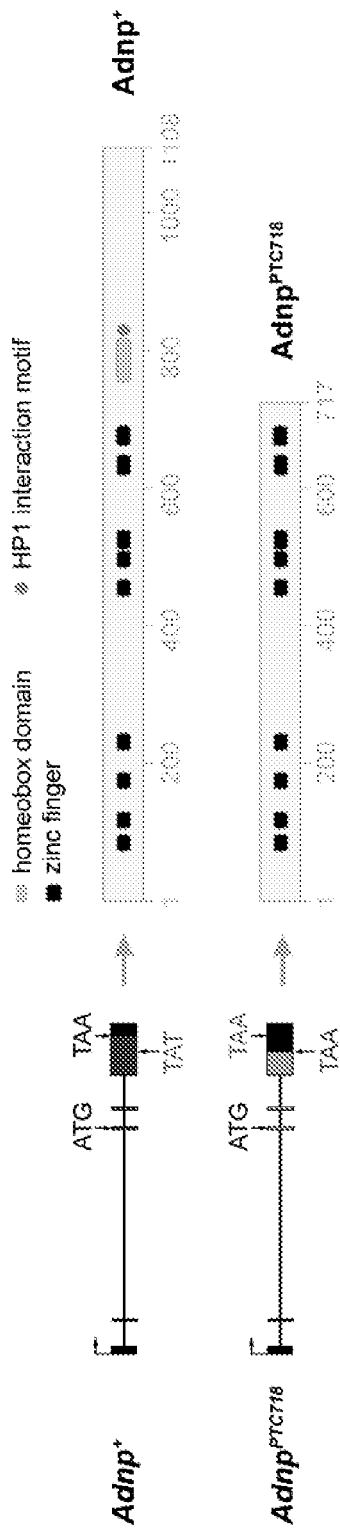
FIG. 3 Nonsense mutations truncate the C-terminus of Adnp. Scheme depicting the wild type and mutant Adnp alleles, which code for Tyr (blue) or a patient-specific premature termination codon (red) at amino acid position 718, respectively. Full length and truncated protein products are shown on the right. Arrow indicates transcription start site. Boxes represent exons. Numbers denote amino acids.

The present invention relates to the novel use of ribosomal read-through compounds for the prevention and/or treatment Autism Spectrum Disorder (ASD). In one embodiment, the present invention relates to the use of ribosomal read-through compounds for the treatment and/or prevention of Autism Spectrum Disorder.

Selected terms are defined below and throughout the application. Compounds of the present invention are described using standard nomenclature. Unless defined otherwise, all technical and scientific terms used herein have the same meaning as is commonly understood by one of skill in the art to which this invention belongs. The following general definitions shall apply in this specification, unless otherwise specified:

As used herein, the terms "a" and "an" and "the" and similar references in the context of describing the invention are to be construed to cover both the singular and the plural, unless otherwise indicated herein or clearly contradicted by context. Where the plural form is used for compounds, salts, and the like, this is taken to mean also a single compound, salt, or the like.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values. When describing a dosage herein as "about" a specified amount, the actual dosage can vary by up to 10% from the stated amount: this usage of "about" recognizes that the precise amount in a given dosage form may differ slightly from an intended amount for various reasons without materially affecting the in vivo effect of the administered compound.

The terms "comprising" and "including" are used herein in their open-ended and non-limiting sense unless otherwise noted.

As used herein, the terms "subject" and "patient" are used herein interchangeably to refer to an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an embryo, fetus, infant, child, adolescent or adult.

The term "Autism Spectrum Disorder" ("ASD") as used herein refers to a group of developmental disabilities that can cause significant social, communication and behavioral challenges. Examples of autistic spectrum disorder include, but are not limited to, autistic disorder (classic autism), Asperger syndrome, and pervasive developmental disorder (PSD; atypical autism).

As used herein, the term "subject in need of the treatment" refers to a subject expressing or suffering from Autism Spectrum Disorder. An appropriately qualified person is able to identify such an individual in need of treatment using standard behavioral testing protocols/guidelines. The same behavioral testing protocols/guidelines can also be used to determine whether there is improvement to the individual's disorder and/or symptoms.

The phrase "subject in need of such treatment" as used herein refers to a patient who displays symptoms of autism or an autism spectrum disorder or who will otherwise benefit from the described treatment, including, without limitation, one who (i) will receive treatment with the composition of the invention; (ii) is receiving the composition of the invention; or (iii) has received the composition of the invention. In some other embodiments, the phrase "subject in need of such treatment" also is used to refer to a patient who (i) will suffer from autism or an autism spectrum disorder; (ii) is suffering from autism or an autism spectrum disorder; or (iii) has suffered from autism or an autism spectrum disorder. In some other embodiments, the phrase "subject in need of such treatment" also is used to refer to a patient who (i) will be administered a composition of the invention; (ii) is receiving a composition of the invention; or (iii) has received a composition of the invention, unless the context and usage of the phrase indicates otherwise.

As used herein, the term "Helsmoortel-van der Aa syndrome" ("HVDAS") (OMIM #615873) refers to Autism Spectrum Disorder caused by heterozygous mutations in the ADNP gene on chromosome 20q13.

As used herein, the term "Sifrim-Hitz-Weiss syndrome" also known as sihiwes, refers to Autism Spectrum Disorder associated with CHD4 (Chromodomain Helicase DNA Binding Protein 4)).

As used herein, the term "ADNP" refers to gene Activity-dependent neuroprotector homeobox located at Genomic coordinates (GRCh38): 20:50,888,917-50,934,983 (NCBI) on chromosome 20q13. The gene is also referred to as ADNP1, KIAA0784, HVDAS, MRD28, Activity-Dependent Neuroprotective Protein, Activity-Dependent Neuroprotector, ADNP Homeobox and Activity-Dependent Neuroprotector Homeobox Protein. ADNP is a homeodomain-containing zinc finger protein with putative transcription factor activity and it is essential for embryonic development. However, its precise role in transcriptional regulation and development is not understood. In the mouse, Adnp was shown to interact with the chromatin remodeler Chd4 and the heterochromatin protein HP1 to form a stable complex termed "ChAHP". Genetic ablation of ChAHP components or DNA binding sites in mouse embryonic stem cells prematurely activates lineage-specific genes, revealing an important role for Adnp in restraining the differentiation capacity of pluripotent cells. Adnp targets the ChAHP complex to specific sequence motifs at euchromatic loci, representing an H3K9 methylation-independent mechanism of HP1 recruitment and gene silencing. ADNP was reported to interact with SWI/SNF chromatin remodeling factors in human HEK293 human embryonic kidney cells, suggesting that the chromatin remodeling activity of ChAHP is essential and conserved but that the factor conferring such activity to the complex might be interchangeable depending on tissue type. Furthermore, ChAHP is a conserved protein complex that is not restricted to pluripotent cells. Such a potentially general role of ChAHP in governing cell fate plasticity may explain why ADNP mutations contribute to cancer progression and why several organs and functions of the body are affected in ASD patients with mutations in ADNP (Ostapcuk et al, 2017, Manuscript submitted).

As used interchangeably herein, the terms "premature termination codon" ("PTC"), "premature stop codon", "nonsense codon", "nonsense mutation" and "premature translation termination codon" refers to the result of a mutation that changes a codon corresponding to an amino acid to a stop codon. Such codons, consisting of three nucleotides, when read by a translating ribosome, signal the ribosome to cease translation of the polypeptide and refer to stop codons that occur abnormally in an mRNA, usually upstream of the normal stop codon. PTCs may result in the translation of a shortened polypeptide, or in degradation of the mRNA, as described elsewhere herein.

As used herein, the term "frameshift mutation" means a deletion or insertion of 1, 2 or more nucleotides (other than a multiple of 3) that results in the remaining downstream sequence being transcribed or translated out of phase.

As used herein, the term "missense mutation" is intended to mean a change of a nucleotide within a gene sequence that results in a change in the meaning of a codon, thereby changing the coded amino acid.

As used herein, the term "nonsense-mediated decay" ("NMD") refers to a cellular mechanism that selectively degrades faulty messenger RNA ("mRNA") containing an out-of-place stop (nonsense) codon. Regardless of their "normal" decay rates, mRNAs transcribed from genes that harbor nonsense mutations (dubbed "nonsense-containing mRNAs") are degraded very rapidly. Such "nonsense-mediated mRNA decay" is ubiquitous, i.e., it has been observed in all organisms tested, and leads to as much as ten-to one hundred-fold reduction in the abundance of specific mRNAs. The combination of severely reduced mRNA abundance and prematurely terminated translation causes reductions in the overall level of expression of specific genes that are as drastic as the consequences of gene deletion. The importance of nonsense-mediated mRNA decay to human health is illustrated by the identification of a growing number of inherited disease in which nonsense mutations cause the disease state and in which the respective mRNAs have been shown to be substrates of the nonsense-mediated mRNA decay pathway.

As used herein, the terms "nonsense codon suppression" and "nonsense codon suppressing" refer to the inhibition or suppression of premature translation and/or nonsense-mediated mRNA decay.

As used herein, the phrase "modulation of premature translation termination and/or nonsense-mediated mRNA decay" refers to the regulation of gene expression by altering the level of nonsense codon suppression. For example, if it is desirable to increase production of a functional read-through protein encoded by a gene with a premature stop codon, i.e., to permit read-through of the premature stop codon of the disease gene so translation of the RNA can occur, then modulation of premature translation termination and/or nonsense-mediated mRNA decay entails up-regulation of nonsense codon suppression. Conversely, if it is desirable to promote the degradation of an mRNA with a premature stop codon, then modulation of premature translation termination and/or nonsense-mediated mRNA decay entails downregulation of nonsense codon suppression.

As used herein, the terms "nonstop decay", "nonstop degradation", or "NSD" refer to the pathway for the degradation of mRNA transcripts that do not contain any in-frame stop codons. Nonstop decay is a cellular mechanism of mRNA surveillance to detect mRNA molecules lacking a stop codon and preventing these mRNAs from translation. Compounds have been described that inhibit nonstop mRNA degradation of mRNA, e.g., in US20040072201, which is hereby incorporated by reference.

As used herein, the terms "readthrough compound" ("RTC"), "compound that induces readthrough of PTCs", "compound having nonsense codon suppressing activity", "nonsense codon suppressor agent" and "nonsense codon suppressor" refer to any compound, or pharmaceutically acceptable salt, prodrug, solvate, hydrate, polymorph or enantiomer thereof, that, when applied to and/or present in a cell, induces ribosomes to read a stop codon, e.g., a PTC, as coding for an amino acid and which can cause the read-through of a nonsense codon in vitro or in vivo and produce full-length protein(s). To date, most reported PTC read-through compounds (RTCs) that are active in mammalian cells belong to the aminoglycoside antibiotics class (e.g., gentamicin, paromomycin, G418 and its derivatives NB74 and NB84) (Zingman et al. 2007). Certain types of aminoglycosides can induce ribosomes to read through PTC mutations via insertion of a random amino acid by near-cognate transfer RNA. The therapeutic potential of aminoglycosides has been evaluated in the laboratory for different genetic models, such as cystic fibrosis (Du et al. 2002), muscular dystrophy (Loufrani et al. 2004), Hurler syndrome (Keeling et al. 2001), cystinosis (Helip-Wooley et al. 2002), spinal muscular atrophy (Sossi et al. 2001), ataxia-telangiectasia (Lai et al. 2004), and type 1 Usher syndrome (Rebibo-Sabbah et al. 2007).

As used herein, the term "full-length" in the context of a functional read-through protein refers to a functional read-through protein that is composed of the same number of amino acid residues as the corresponding wild-type protein.

As used herein, the term "non-wild-type protein" refers to a protein having an amino acid sequence that is different from the corresponding wild-type protein.

As used herein, the term "wild-type" in the context of a protein refers to a protein that is found in nature (often (but not necessarily) it is the predominant protein) and is designated as a standard or reference protein.

As used herein, the phase "functional read-through protein" refers to a functional protein produced as a result of read-through of a nonsense codon in an RNA (e.g., mRNA) transcribed from a gene.

As used herein, the term "functional" in the context of a functional read-through protein refers to a protein that has enough of the functions of the corresponding wild-type protein to have a beneficial effect in a cell or subject which does not produce or produces insufficient amounts of the wild-type protein as a result of a mutation (e.g., a nonsense mutation) in the nucleic acid sequence (e.g., gene) encoding the protein.

As used herein, the phrases "disease associated with a nonsense mutation in a gene(s)" and "disorder associated with a nonsense mutation in a gene(s)" are used interchangeably to refer to a disease that results from, directly or indirectly, nonsense mutation(s) in a gene, where the nonsense mutation(s) prevents production of a wild-type protein in an affected cell. Diseases associated with a nonsense mutation encompass diseases in which a single gene contains one, two, three or more nonsense mutations as well as diseases in which two, three or more (multiple) genes contain one, two, three or more nonsense mutations.

As used herein, the term "treatment" refers to a clinical intervention made in response to a disease, disorder or physiological condition manifested by a patient, particularly a patient suffering from ASD. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may improve behavioral performance of the subject, including ASD-related behaviors. As used herein, the term "prevention" refers to any activity that reduces the burden of the individual later expressing those behavioral symptoms. This takes place at primary, secondary and tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

As used herein the term "agent" is understood to mean a substance that produces a desired effect in a tissue, system, animal, mammal, human, or other subject. It is also to be understood that an "agent" may be a single compound or a combination or composition of two or more compounds.

The pharmaceutical compositions of the invention may include a "therapeutically effective amount", "effective amount" or a "prophylactically effective amount" of a compound described herein. The term "pharmaceutically effective amount", "therapeutically effective amount" or "clinically effective amount" of a single therapeutic agent or of a combination of therapeutic agents is an amount sufficient, at dosages and for periods of time necessary, to provide an observable or clinically significant improvement over the baseline of clinically observable signs and symptoms of the disorders treated with the combination. A therapeutically effective amount may vary according to factors such as the disease state, age, sex, and weight of the individual. A therapeutically effective amount is also one in which any toxic or detrimental effects of the therapeutic agents are outweighed by therapeutically beneficial effects. A "therapeutically effective dosage" preferably modulates a measurable parameter in a desired manner. The ability of a compound to desirably modulate a measurable parameter can be evaluated in an animal model system predictive of efficacy in humans to help establish suitable dosing levels and schedules. Alternatively, this property of a composition can be evaluated by examining the ability of the compound to modulate an undesired parameter by using in vitro assays known to the skilled practitioner.

As used herein, a "therapeutic protocol" or "prophylactic protocol" refers to a regimen of timing and dosing of one or more therapies. A used herein, a "protocol" includes dosing schedules and dosing regimens. It may include executing a protocol, which may include administering one or more drugs to a patient (human or otherwise), in an effort to alleviate signs or symptoms of the disease. In certain embodiments, therapeutic treatment prevents worsening of a disease or condition.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Within the meaning of the present disclosure, the term "protect" is used herein to mean prevent, delay, or treat, or all, as appropriate, development, continuance or aggravation of a disease in a subject, e.g., a mammal or human. The term "prevent", "preventing" or "prevention" as used herein comprises the prevention of at least one symptom associated with or caused by the state, disease or disorder being prevented.

The term "inhibition", "inhibitor," or "antagonist" includes a reduction in a certain parameter, e.g., an activity, of a given molecule or pathway.

In some embodiments, the subject suffers from autism. In some embodiments, the subject suffers from ASD. In some embodiments, the subject suffers from Helsmoortel-van der Aa syndrome. In one embodiment, it has been determined through pre-screening that the patient possesses a mutation in gene ADNP. In another embodiment, it has been determined through pre-screening that the patient has a premature stop codon (i.e., UAA, UGA, or UAG). In another embodiment, it has been determined through pre-screening that the patient has a mutation resulting in a frameshift. In another embodiment, it has been determined through pre-screening that the patient has a mutation resulting in a missense mutation. In another embodiment the mutation is in the ADNP gene on human chromosome 20. Mutations in ADNP gene are selected from the group comprised in table 1.

| Allele Change | Residue Change | Variant Type |
|---|---|---|
| — | p.Thr443Ala | missense_variant |
| c.1046_1047delTG | p.Leu349ArgfsTer49 | frameshift_variant |
| c.118C > T | p.Gln40Ter | stop_gained |
| c.1211C > A | p.Ser404Ter | stop_gained |
| c.1222_1223delAA | p.Lys408ValfsTer31 | frameshift_variant |
| c.1222_1224delAAGinsG | p.Lys408ValfsTer31 | frameshift_variant |
| c.1553G > A | p.Arg518His | missense_variant |
| c.1668G > C | p.Gln556His | missense_variant |
| c.1930C > T | p.Arg644Ter | stop_gained |
| c.2153_2165delCTTACGAGCAAAT | p.Thr718GlyfsTer12 | frameshift_variant |
| c.2156_2157insA | p.Tyr719Ter | frameshift_variant |
| c.2157C > G | p.Tyr719Ter | stop_gained |
| c.2157del | p.Tyr719Ter | frameshift_variant |
| c.2157delCinsAC | p.Tyr719Ter | frameshift_variant |
| c.2188C > T | p.Arg730Ter | stop_gained |
| c.2188C > T | p.Arg730Ter | stop_gained |
| c.2213C > G | p.Ser738Ter | stop_gained |
| c.2288C > T | p.Ser763Phe | missense_variant |
| c.2318_2319del | p.Lys773fs | frameshift_variant |
| c.2490_2494delATTAAinsA | p.Leu831IlefsTer82 | frameshift_variant |
| c.2491_2494delTTAA | p.Lys831IlefsTer81 | frameshift_variant |

-continued

| Allele Change | Residue Change | Variant Type |
| --- | --- | --- |
| c.2491_2494delTTAA | p.Lys831IlefsTer81 | frameshift_variant |
| c.2491_2499delTTAAATAAAinsTTAAA | p.Asn832LysfsTer81 | frameshift_variant |
| c.2495_2499delATAAAinsA | p.Asn832LysfsTer81 | frameshift_variant |
| c.2496_2499delTAAA | p.Asp832LysfsTer80 | frameshift_variant |
| c.2808delC | p.Tyr936Ter | frameshift_variant |
| c.2866_2869del | p.Glu956fs | frameshift_variant |
| c.2881G > T | p.Asp961Tyr | missense_variant |
| c.3047dup | p.Ala1017GlyfsTer6 | frameshift_variant |
| c.3066_3072delCAGAGAGinsCAG | p.Arg1023SerfsTer3 | frameshift_variant |
| c.3170T > A | p.Leu1057Ter | stop_gained |
| c.3280_3281insCC | p.Gly1094ProfsTer5 | frameshift_variant |
| c.3281G > T | p.Gly1094Val | missense_variant |
| c.632T > A | p.Leu211Ter | stop_gained |
| c.642_649del | p.Asn214fs | frameshift_variant |
| c.673C > T | p.Arg225Ter | stop_gained |
| delTGAC | — | frameshift_variant |
| c.2495_2500delATAAAGinsAG | p.Asn832LysfsTer81 | frameshift_variant | fs = frameshift, del = deletion, ins = insertion, dup = duplication.

In other embodiments it is therapeutically sufficient to decrease the symptoms of ASD by combination therapy in which ASD symptoms are decreased by both NMD inhibition, in particular NMD inhibition of Adnp comprising a PTC and by suppressing nonsense codon recognition. Non-limiting examples of compounds capable of suppressing nonsense codon recognition are embodied by select aminoglycoside antibiotics as described herein or non-aminoglycoside compounds as described herein. These compounds cause ribosomal read-through at the site of the nonsense stop codon in defective mRNA, but are themselves either ineffective or inconsistently effective for treatment of ASD due to the efficient NMD-mediated destruction of defective mRNA in at least a large subset of ASD-relevant cells. However, if NMD-mediated destruction of defective RNA is rendered inefficient (e.g. by downregulation of NMD), read-through-enhancing drugs cause synthesis of full-length protein and mitigation of symptoms of ASD.

In one embodiment, the inhibition or suppression of premature translation and/or nonsense-mediated mRNA decay is in vivo, in particular premature translation and/or nonsense-mediated mRNA decay of Adnp comprising a PTC. In another embodiment, the inhibition or suppression of premature translation and/or nonsense-mediated mRNA decay is in vitro, in particular premature translation and/or nonsense-mediated Adnp mRNA.

In a specific embodiment, the phrase "functional read-through protein" refers to a functional protein produced as a result of read-through of a nonsense codon in an RNA transcribed from a gene comprising a nonsense mutation. In a preferred embodiment, the gene is ADNP. In certain embodiments, the functional read-through protein is composed of the same amino acid sequence as the corresponding wild-type protein encoded by a gene without a nonsense mutation. In other embodiments, the functional read-through protein is a functional non-wild-type protein. In a preferred embodiment the protein is Adnp.

The production of a functional read-through protein(s) encoded by a nucleic acid sequence comprising a nonsense mutation is useful: (i) in subjects that do not express a sufficient amount of the corresponding wild-type protein(s), in particular Adnp, and/or (ii) in subjects that could benefit from the expression of a particular functional read-through protein(s), in particular Adnp.

In certain embodiments, the non-wild-type protein only differs from the corresponding wild-type protein at the amino acid residue(s) in the non-wild-type protein that was inserted at the position(s) encoded by a premature termination codon. In other embodiments, the non-wild-type protein differs from the corresponding wild-type protein: (i) at an amino acid residue(s) in the non-wild-type protein(s) that was inserted at the position encoded by a premature termination codon; and (ii) at an amino acid residue(s) in the non-wild-type protein other than those encoded by a premature termination codon. In a preferred embodiment, the protein is Adnp.

In one aspect, the invention provides methods for producing in a subject (preferably, a human) in need thereof a functional read-through protein(s), in particular Adnp, encoded by a nucleic acid sequence, in particular Adnp, comprising a nonsense mutation(s), the methods comprising administering to the subject an effective amount of a nonsense codon suppressor agent(s). In a specific embodiment, the functional read-through protein(s) corresponds to a wild-type protein, in particular Adnp, that has a beneficial effect in a subject. In certain embodiments, the subject administered the agent(s) does not produce a sufficient amount of the wild-type protein(s), in particular Adnp, that corresponds to the functional read-through protein(s) before administration of a read-through compound. In a specific embodiment, the subject administered the agent(s) has a disease associated with insufficient production of the wild-type protein(s), in particular Adnp, that corresponds to the functional read-through protein. In certain embodiments of the invention, the subject that is going to receive a nonsense codon suppressor agent(s) is screened before receiving the agent(s). In a specific embodiment, the subject is screened to determine if the agent(s) will produce a functional read-through protein(s). In another embodiment, the subject is screened to determine the effective amount of the agent(s) to administer to the subject.

In one embodiment, the present invention provides methods of treating genetic disorders, in particular ASD; which comprise administering a therapeutically effective amount of a pharmaceutical composition comprising a compound that induces read-through of PTCs to a subject (e.g., a mammal such as a human).

While the anticodons of aminoacyl transfer RNAs (tRNAs) recognize sense codons, leading to the incorporation of a specific amino acid, there are no eukaryotic tRNAs with anticodons that match any of the three stop (nonsense) codons UAA, UGA and UAG. Translation termination occurs when a stop codon enters the A site of the ribosome and is controlled essentially by the release factor eRF1.

The antibiotics belonging to the group of aminoglycosides are known to interfere with the decoding center of the ribosomal RNA (rRNA). These antibiotics cause misreading of the RNA code and can allow the insertion of alternative amino acids at the site of a stop codon and this aminoglycoside-induced stop codon read-through may lead to expression of a gene containing a nonsense mutation. In certain embodiments, the nonsense codon suppressor agent used in accordance with the invention is an aminoglycoside. Non-limiting examples of aminoglycosides include gentamicin, streptomycin, amikacin, kanamycin, tobramycin, netilmicin, neomycin, framycetin, negamycin, paromomycin, hygromycin B, apramycin, dihydrostreptomycin, sisomicin, erythromycin, NPC-14 (arbekacin), ELX-02, G-418, ribostamycin, bekanamycin, dibekacin, spectinomycin and derivatives and analogs thereof. In specific embodiments, the nonsense codon suppressor agent used in accordance with the invention is one more from the group comprising gentamicin, streptomycin, amikacin, kanamycin, tobramycin, netilmicin, neomycin, framycetin, negamycin, paromomycin, hygromycin B, apramycin, dihydrostreptomycin, sisomicin, erythromycin, NPC-14 (arbekacin), ELX-02, G-418, ribostamycin, bekanamycin, dibekacin, spectinomycin and derivatives and analogs thereof. In other embodiments, the nonsense codon suppressor agent is used in accordance with the invention is from the group comprising chloramphenicol, azidamfenicol, thiamphenicol and florfenicol and derivatives or analogs thereof that retain activity in promoting read-through of a premature termination codon. In other embodiments, the nonsense codon suppressor agent used in accordance with the invention is an oxazolidinone. Non-limiting examples of oxazolidinones are linezolid, eperzolid, posizolid, radezolid, ranbezolid, sutezolid, tedizolid and analogs or derivatives thereof. In another embodiment, the nonsense codon suppressor agent is used in accordance with the invention is from the group comprising linezolid, eperzolid, posizolid, radezolid, ranbezolid, sutezolid, tedizolid and analogs or derivatives thereof. In certain embodiments, the nonsense codon suppressor agent used in accordance with the invention is a non-aminoglycoside based read-through compounds. Non-limiting examples of non-aminoglycoside based read-through compounds include PTC124 (also referred to as "Ataluren" and marketed under the name Translarna™), RTC 13, RTC 14, amlexanox and tylosin. In specific embodiments, the nonsense codon suppressor agent used in accordance with the invention is from the group comprising PTC124 (ataluren), RTC 13, RTC 14, amlexanox and tylosin. In certain embodiments, a nonsense codon suppressor agent used in accordance with the invention produces an amount of 5%, 10%, 15%, 20%, 25%, 30%, 35%, 40%, 45%, 50%, 55%, 60%, 65%, 70%, 75%, 80%, 85% or 90% or 95% or more of functional read-through protein compared to a cell producing wild-type protein. In some embodiments, a nonsense codon suppressor agent used in accordance with the invention produces an amount of 5-95%, 10%-95%, 25%-95%, or 10%-65% more of functional read-through protein compared to a cell producing wild-type protein. In one embodiment in accordance with the invention, nonsense codon suppressor agent is used for treating and/or preventing Autism spectrum disorder (ASD). In one embodiment ASD is caused by one or more non-sense mutations in gene ADNP. In one embodiment, the one or more mutations in gene ADNP are selected from the group comprising c.1046_1047delTG, c.118C>T, c.1211C>A, c.1222_1223delAA, c.1222_1224delAAGinsG, c.1553G>A, c.1668G>C, c.1930C>T, c.2153_2165delCTTACGAGCAAAT, c.2156_2157 insA, c.2157C>G, c.2157del, c.2157delCinsAC, c.2188C>T, c.2213C>G, c.2288C>T, c.2318_2319del, c.2490_2494delATTAAinsA, c.2491_2494delTTAA, c.2491_2499delTTAAATAAAinsTTAAA, c.2495_2499delATAAAinsA, c.2496_2499delTAAA, c.2866_2869del, c.2881G>T, c.3047dup, c.3066_3072delCAGAGAGinsCAG, c.3170T>A, c.3280_3281insCC, c.3281G>T, c.632T>A, c.642_649del, c.673C>T, delTGAC, c.2495_2500delATAAAGinsAG. In another embodiment, the mutation in gene ADNP results in pre-mature termination during translation of the protein. Said pre-mature termination can be the result of a mutation converting an amino acid codon into a stop codon, or the result of a missense variant. Accordingly, mutations in the protein Adnp are selected from the group comprising p.Thr443Ala, p.Leu349ArgfsTer49, p.Gln40Ter, p.Ser404Ter, p.Lys408ValfsTer31, p.Arg518His, p.Gln556His, p.Arg644Ter, p.Thr718GlyfsTer12, p.Tyr719Ter, p.Arg730Ter, p.Ser738Ter, p.Ser763Phe, p.Lys773fs, p.Leu831IlefsTer82, p.Lys831IlefsTer81, p.Asn832LysfsTer81, p.Asp832LysfsTer80, c.2808delC, p.Glu956fs, p.Asp961Tyr, p.Ala1017GlyfsTer6, p.Arg1023SerfsTer3, p.Leu1057Ter, p.Gly1094ProfsTer5, p.Gly1094Val, p.Leu211Ter, p.Asn214fs, p.Arg225Ter.

As described elsewhere herein, compounds that induce read-through of PTCs are useful for the treatment of genetic diseases caused by PTCs because they allow the translation past the mutant stop codon or past the missense mutation. However, because these compounds allow read-through of all stop codons, they result in mRNAs that effectively have no stop codons, resulting in induction of the nonstop mediated mRNA decay pathway (NSD), degradation of the mRNA, and no translated protein. Therefore, the use of compounds inhibiting NSD will prevent degradation of the mRNAs, and will allow compounds that induce read-through of PTCs to have clinical effectiveness in the treatment of genetic disorders. In one embodiment, the present invention provides methods of treating genetic disorders which comprise administering a therapeutically effective amount of a pharmaceutical composition comprising a nonsense codon suppressor agent, as described herein, and a therapeutically effective amount of a compound that inhibits nonstop mediated mRNA decay pathways (NSD) to a subject (e.g., a mammal such as a human). In one embodiment, the nonsense codon supressor agent is selected from the group comprising gentamicin, streptomycin, amikacin, kanamycin, tobramycin, netilmicin, neomycin, framycetin, negamycin, paromomycin, hygromycin B, apramycin, dihydrostreptomycin, sisomicin, erythromycin, NPC-14 (arbekacin), ELX-02, G-418, ribostamycin, bekanamycin, dibekacin, spectinomycin and derivatives and analogs thereof. In another embodiment, the nonsense codon suppressor agent is selected from the group comprising chloramphenicol, azidamfenicol, thiamphenicol and florfenicol and derivatives or analogs thereof. In another embodiment, the nonsense codon suppressor agent is selected from the group comprising linezolid, eperzolid, posizolid, radezolid, ranbezolid, sutezolid, tedizolid and analogs or derivatives thereof. In another embodiment, the nonsense codon suppressor agent is selected from the group comprising PTC124 (ataluren), RTC 13, RTC 14, amlexanox and tylosin.

Also within the scope of the invention is a kit comprising as therapeutic agents a nonsense codon suppressor agent as described herein, together with one or more other elements: instructions for use such as dosage and administration instructions; other reagents for use; devices or other materials for preparing the compound for administration, such as a mixing container; pharmaceutically acceptable carriers; and devices or other materials for administration to a subject, such as a syringe. Said dosage and administration instructions can be of the kinds that are provided to a doctor, for example by a drug product label, or they can be of the kinds that are provided by a doctor, such as instructions to a patient;

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

The Examples below are set forth to aid in the understanding of the invention but are not intended, and should not be construed, to limit its scope in any way.

Methods

Cell Culture and Genome Editing

Mouse embryonic stem cells (129×C57Bl/6;[32] were cultured on gelatin-coated dishes in mES medium containing DMEM (Gibco 21969-035), supplemented with 15% fetal bovine serum (Gibco), 1× non-essential amino acids (Gibco), 1 mM sodium pyruvate (Gibco), 2 mM L-glutamine (Gibco), 0.1 mM 2-mercaptoethanol (Sigma), 50 mg/ml penicillin, 80 mg/ml streptomycin, 3 uM GSK inhibitor (Calbiochem, D00163483), 10 uM MEK inhibitor (Tocris, PD0325901), and home-made LIF, at 37° C. in 5% $CO_2$.

The genome editing was performed as previously published[7] in the absence of GSK and MEK inhibitors in the above-described mES medium.

Generation of Endogenously Tagged mESC Lines

For endogenous gene tagging using TALENs, Rosa26: BirA-V5-expressing cells (cMB053 or cMB063) were transfected with 400 ng of TALEN-EED, 400 ng of TALEN-KKR, 100 ng of pRRP reporter and 1000 ng of donor ssODN encoding for the tag sequence. All transfections were carried out using Lipofectamine 3000 reagent (Invitrogen) at 3 μl/1 μg DNA ratio in OptiMEM medium (Invitrogen). Transfected cells were selected by adding Puromycin (2 μg/ml) to the mES medium 24 hr post-transfection. After 36 hrs of selection, surviving cells were sparsely seeded for clonal expansion, then the clones were individually picked, split and screened by western blot for desired tag integration.

Straight KO mESC Lines Generation $Cbx1^{-/-}$ mESCs were generated using TALENs targeting the first and last coding exon, resulting in deletion of approx. 6000 bp (exon 2-exon 6).

$Adnp^{-/-}$ mESCs were generated using Cas9 and TALENs targeting the first and last coding exon, resulting in deletion of approx. 7000 bp (exon 2-exon 4). The Cas9-sgRNA sequence was cloned into SpCas9-2A-mCherry plasmid (Knuckles et. al, *NSMB*, 2017).

Conditional mESC Lines Generation

The $Cbx3^{fl/fl}$ cell line was generated according to[7]. For the $Cbx5^{fl/fl}$ conditional cell line, a mouse ES cell line harboring an integration of the CreERT2 recombinase fusion in the Rosa26 locus (cMB052 or cMB063) was transfected with TALENSs cutting before and after the third exon. ssODNs with corresponding homology arms and LoxP sites for integration were also included in the transfection mix. Clones were screened for homozygous integrations for both LoxP sites. A cell line with both bi-allelic LoxP integrations was tested for recombination efficiency by treating the cells with 0.1 μM 4-hydroxytamoxifen (4OHT, Sigma) followed by western blot or qRT-PCR.

Western Blotting

Cells were grown to confluency on 6 well plates, collected in PBS, pelleted by 2 min centrifugation at 400 g, and pellets were resuspended in 1000 μl protein extraction buffer (50 mM Tris-HCl [pH 7.5], 150 mM NaCl, 1% Triton X-100, 0.5 mM EDTA, and 5% glycerol) supplemented with PIC (Roche), 1 mM PMSF, and 1 mM DTT. Proteins were extracted for 30 min on ice, the lysates were centrifuged at 16,000 g for 20 min at 4° C., and protein concentration in the supernatant was determined using the BioRad protein assay. For western blotting, 20 μg of protein were resolved on NuPAGE-Novex Bis-Tris 4-12% gradient gels (Invitrogen), semi-dry transferred on polyvinylidene fluoride (PVDF) membrane, blocked for 30 min in 2.5% non-fat dry milk in TBS-0.05% Tween 20 (TBST), and stained with primary antibodies at 4° C. overnight. The primary antibodies used for western blotting were mouse anti-FLAG (1:1000, Sigma clone M2), goat-anti-HP1α (1:1000, Abcam, ab77256), mouse-anti-HP1α (1:1000, Millipore, mab3446), rat-anti-HP1gamma (1:500, Serotec, MCA1946), mouse-anti-HP1α (1:2000, Cell Signaling Technology), mouse-anti-Chd4 (1:1000, Abcam, ab70469), rabbit-anti-Mta2 (1:1000, Bethyl, A300-395A-T), rabbit-anti-Gatad2b (1:1000, Bethyl, A301-283A-T), rabbit-anti-Mbd3 (1:1000, Bethyl, A302-528A-T) and rat-anti-tubulin (1:5000, Abcam clone YL1/2). Signal was detected with corresponding HRP-conjugated secondary antibodies and Immobilon Western Chemiluminiscent HRP Substrate (Millipore). For streptavidin staining, membranes were blocked after transfer in 2% BSA in TBST and incubated with streptavidin-HRP (1:20, 000, Sigma) for 30 min at room temperature, followed by signal development as above.

Chromatin Immunoprecipitation

A confluent 10 cm culture dish of ESCs (ca. 2×10[7] cells) was cross-linked for 7 min RT with 1% final formaldehyde solution (Sigma, F8775) added directly to the mES medium. Cross-linking was quenched by addition of glycine to a final concentration of 0.125 mM and incubation at 4° C. for 10 minutes; cells were then washed twice with PBS. Cells were collected in 1 ml PBS with Proteinase Inhibitor Cocktail (PIC, Roche) and spun at 600 g for 5 min at 4° C. Cells were then resuspended in 5 ml/dish Wash Solution I (10 mM TRIS pH:8, 10 mM EDTA, 0.5 mM EGTA, 0.25% Triton X-100), incubated 10 min on ice and spun at 1200 g for 5 min at 4° C. Remaining nuclear pellet was then resuspended in 5 ml/dish Wash Solution II (10 mM TRIS pH:8, 1 mM EDTA, 0.5 mM EGTA and 200 mM NaCl) and incubated 5 min on ice, then spun at 1200 g for 5 min at 4° C. Cell pellets were subsequently washed in 900 μl/dish Sonication Buffer (10 mM Tris-HCl pH 8.0, 1 mM EDTA, 0.1% SDS) without disturbing the pellet, and finally resuspended in the Sonication Buffer supplemented with PIC. Chromatin was then sonicated in Covaris 1 ml tubes for 15 minutes with the following settings: Duty Cycle: 5%, Peak Incident Power: 140 Watts, Cycles per Burst: 200, temperature (bath): 4° C.

Beads Preparation

For Bio-ChIP, 40 µl/IP of Dynabeads Stepavidin (Thermofisher) or alternatively for Ab-ChIP 40 µl/IP Protein-G Dynabeads (Thermofisher), were washed twice for 5 min in 0.5 ml of Blocking Buffer (PBS, 0.5% Tween, 0.5% BSA). Streptavidin Dynabeads were then washed twice with IP Buffer (50 mM HEPES pH 7.5, 150 mM NaCl, 1 mM EDTA, 0.1% SDS, 0.1% sodium deoxycholate, 1% Triton X100) and stored on ice. Protein-G Dynabeads were incubated for 1 hr at RT in Blocking Buffer with desired antibody. Beads were then washed twice in Blocking Buffer and stored on ice. All ChIP-seq experiments in this work were performed using the Bio-ChIP protocol. For Chd4 ChIP, 10 µg of mouse anti-Chd4 (Abcam, ab70469, 3F2/4) conjugated to Protein-G was used.

Immunoprecipitation (IP) and Washes

10 µl (1%) was kept as input sample. 40 µl pre-blocked Dynabeads were added to 1 ml of sonicated chromatin in IP Buffer and incubated overnight at 4° C. on a rotating wheel. Beads were collected on a magnetic rack for 2-3 min in order to remove supernatant between each step, and washed as follows: for Bio-ChIP twice 10 min with 2% SDS in TE, once 10 min with HSB (50 mM HEPES pH7.5, 1 mM EDTA, 1% Triton X-100, 0.1% Sodium Deoxycholate and 500 mM NaCl), once 10 min with DOC buffer (250 mM LiCl, 0.5%, NP-40, 0.5% deoxycholate, 1 mM EDTA and 10 mM TRIS pH:8) and twice 10 min with 1 ml TE. For Ab-ChIP beads were washed five times with IP Buffer, twice with DOC buffer, and twice with TE buffer. Beads were then resuspended in 300 µl Elution Buffer (1% SDS and 100 mM NaHCO$_3$) and 6 µl RNaseA (10 mg/ml stock) and incubate at 37° C. for 30 min while mixing. Elution buffer was adjusted with 6 µl 0.5 M EDTA, 12 µl 1M TRIS pH8 and 2.5 µl Proteinase K (10 mg/ml, Roche). Beads were incubated 3 hours at 55° C. and then overnight at 65° C. mixing to de-crosslink. Same procedure was followed for input samples including RNAse and Proteinase K digestion. DNA was purified using AMPure XP beads (Beckman Coulter). Quantification was performed with Qubit dsDNA high sensitivity assay (Thermofisher).

ChIP-qPCR and ChIP-Seq

DNA was subjected to qPCR analysis (as described for qRT-PCR, below) using ChIP primers. In case of ChIP-seq sample preparation, library construction was performed using the NEBNext Ultra kit (New England Biolabs) following manufacturer recommendations. Libraries were sequenced on Illumina HiSeq 2500 machines, with 50 bp single-end sequencing.

RT-qPCR and RNA-Seq

For quantitative RT-PCR (qRT-PCR) experiments, total RNA was extracted from mESCs with the Absolutely RNA Microprep Kit (Stratagene). 500 ng of total RNA was reverse transcribed with Primescript RT kit (Clontech). qRT-PCR was performed on a CFX96 Real-Time PCR System (Bio-Rad) using the SsoAdvanced SYBR Green Supermix (Bio-Rad, #172-5264). Relative RNA levels were calculated from $C_T$ values according to the $\Delta C_T$ method and normalized to TBP mRNA levels where applicable. For RNA-seq, briefly total RNA (isolated as described previously) was subjected to ribosomal RNA depletion using the Ribozero kit (Illumina) followed by library construction using the ScriptSeq V2 library preparation kit (Illumina).

Affinity Purification Followed by LC-MS/MS

Cells were grown to confluency on 10 cm dish, collected in PBS, and pelleted by 2 min centrifugation at 400 g. All subsequent steps were performed on ice or at 4 C. Pellets were resuspended in 3 ml of Nuclear extract buffer 1 (NEB1: 20 mM HEPES, 10 mM KCl, 1 mM EDTA, 0.1 mM Na3VO4, 0.2% NP-40, 10% glycerol, 1 mM DTT, 1×PIC) followed by centrifugation at 1000 g for 3 min. Pellets were resuspended in 1 ml NEB1 buffer and incubated on ice for 10 min, followed by dounce homogenization. Isolated nuclei were collected by 15 min centrifugation at 1000 g, and carefully washed twice with 1 ml of NEB1 without disturbing the pellet. Pellets were then resuspended in 0.5 ml of Nuclear extract buffer 2 (NEB2: 20 mM HEPES, 10 mM KCl, 1 mM EDTA, 0.1 mM Na3VO4, 350 mM NaCl, 20% glycerol, 1 mM DTT, 1×PIC), dounce homogenized (20× up and down), incubated for 30 min, and finally spun for 30 min at 16000 g. Protein concentration was determined using Bradford assay, and approximately 250 □g of nuclear extracts were used per affinity purification. The protein lysates were adjusted to Affinity Purification buffer (AP buffer: 350 mM or 500 mM NaCl, 20 mM Tris-HCl pH 7.5, 0.3% NP-40, 1 mM EDTA and 10% glycerol, 1 mM DTT, 1×PIC), added to 20 µl/AP of anti-FLAG-M2 Dynabeads (Sigma), and incubated ON rotating at 4° C. Dynabeads were washed the next day in AP buffer (4×10 min), followed by 3×15 min elution of bound proteins with 3FLAG peptide (final concentration of 0.3 mg·ml$^{-1}$ in AP buffer, Sigma). Next, elutions were pooled and added to the AP washed Stepavidin Dynabeads (Thermofisher), and incubated ON rotating at 4° C. Streptavidin Dynabeads were washed the next day with AP buffer (4×10 min), followed by a wash with AP buffer without NP40. For single step affinity purification, FLAG purification was omitted, and lysates were directly applied to the Streptavidin Dynabeads. The enriched proteins were digested directly on the Dynabeads with 0.1 mg·ml$^{-1}$ trypsin in Digestion buffer (50 mM Tris pH 8.0, 1 mM CaCl$_2$, 1 mM TCEP). The generated peptides were acidified with TFA to a final concentration of 0.8% and analyzed by capillary liquid chromatography tandem mass spectrometry with an EASY-nLC 1000 using the two-column set-up (Thermo Scientific). The peptides were loaded with 0.1% formic acid, 2% acetonitrile in H$_2$O onto a peptide trap (Acclaim PepMap 100, 75 um×2 cm, C18, 3 um, 100 Å) at a constant pressure of 800 bar. Peptides were separated, at a flow rate of 150 nl/min with a linear gradient of 2-6% buffer B in buffer A in 3 minutes followed by an linear increase from 6 to 22% in 40 minutes, 22-28% in 9 min, 28-36% in 8 min, 36-80% in 1 min and the column was finally washed for 14 min at 80% B (Buffer A: 0.1% formic acid, buffer B: 0.1% formic acid in acetonitrile) on a 50 um×15 cm ES801 C18, 2 um, 100 Å column (Thermo Scientific) mounted on a DPV ion source (New Objective) connected to a Orbitrap Fusion (Thermo Scientific). The data were acquired using 120000 resolution for the peptide measurements in the Orbitrap and a top T (3 s) method with HCD fragmentation for each precursor and fragment measurement in the ion trap according the recommendation of the manufacturer (Thermo Scientific). Protein identification and relative quantification of the proteins was done with MaxQuant version 1.5.3.8 using Andromeda as search engine[33] and label free quantification (LFQ.[34]) as described in[35]. The mouse subset of the UniProt version 2015_01 combined with the contaminant DB from MaxQuant was searched and the protein and peptide FDR were set to 0.01. All MaxQuant parameters can be found in the uploaded parameterfile: mqpar.xml. Statistical analysis was done in Perseus (version 1.5.2.6)[33,34,36]. Results were filtered to remove reverse hits, contaminants and peptides found in only one sample. Missing values were imputed and potential interactors were determined using t-test and visualized by a volcano plot. Significance lines corresponding to a given FDR have been determined by a permutation-based method[37]. Threshold values (FDR) were selected between 0.005 and 0.05 and SO (curve bend) between 0.2 and 2 and are shown in the corresponding figures. Results were exported from Perseus and visualized using statistical computing language R.

iBAQ

Intensity based absolute quantification (iBAQ) was done as described in[38] to evaluate protein abundances in the ChAHP complexes of the different pull downs.

Size Exclusion Chromatography of Nuclear Lysates

Nuclear lysates were isolated as described above (Affinity purification) from 3×10 cm dishes of Adnp$^{FLAavi/FLavi}$ mES cells (cMB264). Nuclear lysates were then concentrated to 250 □l final volume using Amicon Ultra 0.5 ml Centrifugical Filters (3 kDa, Millipore), and fractionated by size exclusion chromatography on a Superose 6 HR 10/300 resin by fast protein liquid chromatography (AKTA; Amersham-Pharmacia Biotech). The predicted size exclusion maximum for this resin is 40 MDa, with a void volume of 7.35 ml. The column was equilibrated in 2 column volumes of Gel Filtration buffer (250 mM NaCl, 50 mM Tris-HCl pH 7.5, 1 mM DTT, 1×PIC) prior to sample loading. High-molecular-weight protein column standard was used to define the column resolution (Sigma). Protein peaks were detected by UV monitoring. Thyroglobulin ($M_r$, 669,000) peaked in fraction 9 and 10. Prior to loading, each nuclear lysate was adjusted to the appropriate column conditions and centrifuged at 100,000×g for 30 min. A 200 μl of lysate was loaded onto the column and collected into 350-μl fractions; fractions were then subjected to trichloroacetic acid (TCA) precipitation for Western blot analysis. For TCA precipitation, the sample volume was adjusted to 500 μl with the GF buffer followed by the addition of 50 μl of 0.15% sodium deoxycholate; tubes were vortexed and incubated at room temperature for 10 min. Protein was precipitated by the addition of 25 μl of 100% TCA (Sigma), followed by a 20-min incubation at −20° C. Precipitated proteins were collected by centrifugation at 10,000×g for 10 min at 4 C. Protein pellets were washed with acetone and air-dried. The protein pellet was solubilized in 1× sample buffer (62.5 mM Tris [pH 6.8], 0.72 M β-mercaptoethanol or 0.1 M DTT, 10% glycerol, 2% SDS, and 0.05% bromophenol blue) and resolved by NuPAGE-Novex Bis-Tris 4-12% gradient gels (Invitrogen) and subjected to western blot analysis (see Western blot method section for the further details).

Computational Methods

RNA-Seq Analysis

All sequencing reads were aligned to the December 2011 (mm10) mouse genome assembly from UCSC[39]. HP1-mutant RNA-seq data were aligned using STAR 2.5.0a with the following settings to allow reporting of one randomly chosen alignment per multi-mapping read: "-outFilterMultimapNmax 20 -outMultimapperOrder Random -outSAMmultNmax 1 -alignSJoverhangMin 8 -alignSJDBoverhangMin 1 -outFilterMismatchNmax 999 -alignIntronMin 20 -alignIntronMax 100000 -alignMatesGapMax 100000 -outSAMtype BAM SortedByCoordinate". Aligned and sorted reads were indexed using SAMtools (version 1.2). Adnp-mutant RNA-seq data were aligned in Galaxy using Bowtie with the parameters "-m 1 -best-strata"[40]. Aligned Bam files were imported in R using QuasR (1.14.0)[41].

BigWig files normalized for sequencing depth were generated using the QuasR qExportWig function.

Reads were counted over exons using the qCount function and collapsed to yield one value per gene. This count table was used for differential expression calling with the EdgeR package[42]. For comparing the different Cbx knock-out cell lines with Adnp KO, all biological replicates of the parental/ untreated cell lines for Cbx3 and Adnp were used as control group (ctrl), whereas the respective knock-out replicates were considered the treatment group.

GO Term Analysis

GO term analysis of upregulated gene sets was performed using Metascape[43].

ChIP-Seq Read Alignment

ChIP-seq data were aligned in R using the qAlign function from the QuasR package[41] with default settings, which calls the Bowtie aligner with parameters "-m 1-best-strata"[40]. Depth-normalized BigWig files were generated using QuasR 1.14.0

Peak Finding

Adnp peaks were called on ChIP replicates using the corresponding Inputs as background (all BAM files from QuasR alignment). MACS version 2.1.1.20160309[44] was run with the default parameters. Peaks detected in at least 2 out of 3 replicates were kept.

HP1gamma peaks were called on both wt and Adnp KO ChIP replicates individually, using the corresponding Inputs as background (all BAM files from QuasR alignment). MACS was run with the following options: -nomodel -shift 100 -extsize 200. Subsequently, peak lists were intersected using bedtools intersect. Peaks present in both wt and Adnp KO datasets, which did not contain the top scoring Adnp motif, were defined as Adnp-independent HP1gamma peaks.

Motif Finding

HOMER v.4.8 was used with default settings to identify DNA sequence motifs in Adnp peaks[8].

Heatmaps and Meta Plots

Heatmaps and meta plots were generated from averaged replicates using the command line version of deepTools2[45]. Peak centers were calculated based on the peak regions identified by MACS (see above). BigWig coverage files for individual replicates were generated by QuasR (see above). For averaging replicates and for calculating log 2 ChIP/Input ratios, bigwigCompare from deepTools2 was used. For histone modification meta plots over ChAHP peaks, the inventors used the following previously published data sets: H3K4me1 (GSE27841)[46], H3K4me2 (GSE25532)[47], H3K9ac (GSE31284)[48], H3K9me2 (GSE54412)[49], H3K9me3 (GSE12241)[50]

Repeat Analysis

Repeat masker coordinates for mm10 were downloaded from UCSC table browser (repeat masker 2012 Feb. 7 update). Fasta sequences for all repetitive elements were extracted using bedtools getfasta v2.25.0 (REF) and split up into the respective repeat classes. Repeat class fasta files were deduplicated using dedupe (minidentity=98 minoverlap=20) from BBTools (http://jgi.doe.gov/data-and-tools/bbtools/) and then used to generate a composite STAR index containing all repetitive sequences and individual indices for each repeat class. RNA-seq reads were aligned to the genome and the repeat composite index using STAR 2.5.0a. Alignment scores for each read were compared between the full genome and the repeat composite index and reads with higher or equal score in the repeat composite table were considered as mapping to repetitive sequences. These reads were subsequently mapped against the individual repeat class indices and alignment scores for each read to each repeat class were recorded in a table. Reads were assigned to respective repeat classes based on the highest alignment score. Reads mapping to multiple classes equally good were considered "ambiguous" and not counted. Reads with a STAR alignment score below 30 were considered "unmapped" due to too many mismatches and/or indels. Finally, to compare samples/conditions, read counts per class were normalized to 1 million genome mapping reads.

Biochemistry

Cloning cDNA encoding full length human ADNP (amino acid residues 1-1102) was PCR amplified with primers and cloned into a pFast-Bac-derived vector (Invitrogen) in frame with an N-terminal $His_6$-tag. Plasmids encoding full length or N-terminally truncated Adnp (amino acid residues 229-1102) with a C-terminal StrepII-tag were generated by PCR amplification. The amplified cDNA was cloned into a pAC8-derived vector[51]. Expression constructs encoding full length human HP1☐ (amino acid residues 1-183) were generated by amplification of cDNA and cloning into pFast-Bac-derived vectors in frame with an N-terminal $His_6$- or StrepII-tag. cDNA for individual CD (amino acid residues 11-81) or CSD (amino acid residues 109-183) domains of HP1γ was amplified and cloned into a pAC8-derived vector in frame with an N-terminal $His_6$-tag. cDNA encoding for full length human Chd4 (amino acid residues 1-1912) and cloned into a pAC8-derived vector in frame with an N-terminal $His_6$-tag.

In Vitro Reconstitution of ChAHP

Full length and truncated versions of ChAP subunits were subcloned into pAC8 or pFastBac-derived vectors[51]. The following constructs were generated: human Adnp (amino acid residues 1-1102 or residues 229-1102) with a C-terminal StrepII-tag, N-terminally $His_6$-tagged human Chd4 (isoform 1, residues 1-1912) and N-terminally $His_6$-tagged variants of HP1γ (residues 11-81 or 109-183) were cloned into pAC8-derived vectors. Full length human Adnp (amino acid residues 1-1102) in frame with an N-terminal $His_6$-tag and full length human HP1☐ (residues 1-183) in frame with an N-terminal StrepII-tag were cloned into pFastBac-derived vectors. Baculoviruses were generated in *Spodoptera frugiperda* Sf9 cells using the Bac-to-Bac method for pFast-Bac-derived vectors or by cotransfection with viral DNA for pAC8-based vectors. After 1 round of virus amplification in Sf9 cells, *Trichoplusia ni* High5 cells were infected with the respective Baculovirus (150 μl of virus per 10 ml of High5 cells at a density of $2 \times 10^6$ cells/ml) and harvested 48 h post infection. Cells were lysed by sonication in 50 mM Tris pH 7.5, 300 mM NaCl, 5 mM β-mercaptoethanol, 0.1% TritonX-100, 1 mM PMSF, 1× protease inhibitor cocktail (Sigma-Aldrich). For pulldown experiments, cell lysate of a 15 ml culture was added to 30 μl of Strep-Tactin Sepharose (IBA) or 30 μl of His-tag purification resin (Roche) and incubated for 1 h at 4° C. The beads were washed three times with lysis buffer, supplemented with 30 mM imidazole for his pulldowns. Proteins were eluted by addition of 2× sample buffer (62.5 mM Tris-Cl pH6.8, 2% SDS; 25% glycerol, 0.05% bromophenol blue, 5% β-mercaptoethanol) and analysed by SDS PAGE and Coomassie staining.

For large scale expression of the ChAHP complex, 1 L of High5 cells coinfected with Baculoviruses encoding for $His_6$-tagged Adnp and Strep-tagged HP1γ was combined with 21 of High Five cells expressing $His_6$-tagged Chd4. Cells were lysed in lysis buffer and the cleared lysate was passed over a 50 ml Strep-Tactin Sepharose (IBA) column. The bound complex was eluted in 50 mM Tris-Cl pH 7.5, 100 mM NaCl, 5 mM β-mercaptoethanol, 2.5 mM desthiobiotin and bound to an anion exchange chromatography column (Poros HQ) equilibrated in 50 mM Tris-Cl pH 7.5, 100 mM NaCl, 5 mM β-mercaptoethanol. The bound proteins were eluted using a linear NaCl gradient, concentrated and further purified by size exclusion chromatography (HiLoad Superdex 200 26/600) in 50 mM Hepes-OH pH 7.4, 150 mM NaCl, 0.5 mM TCEP. Fractions containing the ChAHP complex were concentrated and reinjected to a Superdex200 10/300 column equilibrated in the same buffer.

Adnp is at the Core of a Novel Silencing-Complex

Experimental results revealed that Adnp represses transcription in mES cells. Notably, the Adnp protein harbors a P*V*L motif, suggesting that it might interact with proteins of the heterochromatin protein 1 (HP1) family[4,12,13], potentially explaining the repressive activity of Adnp. Alternatively, Adnp might regulate gene activity through interactions with the SWI/SNF (Switch/Sucrose Non-Fermentable) chromatin remodeling complex, components of which co-immunoprecipitate with Adnp in HEK293 cells[14]. To unambiguously identify Adnp-interacting proteins in mES cells, the inventors subjected endogenously FLAG-Avi-tagged Adnp to tandem-affinity purification coupled to liquid chromatography tandem mass spectrometry (TAP-LC-MS/MS). Besides Adnp, we observed highly significant enrichment of HP1beta, HP1gamma, and Chd4 (chromodomain helicase DNA-binding domain protein 4), but not SWI/SNF complex subunits. Importantly, these interactions were preserved even under 500 mM NaCl, showing that Adnp stably interacts with Chd4 and the HP1beta and HP1gamma proteins in mES cells.

To elucidate this further, the inventors endogenously tagged the Chd4 gene as well as the Cbx1, Cbx3, and Cbx5 genes, which encode the three mammalian HP1 isoforms HP1beta HP1gamma and HP1alpha respectively, with a FLAG-Avi tag in the same parental mES cells that were used to investigate Adnp[7]. Validating this approach, TAP-LC-MS/MS revealed that all three HP1 isoforms co-precipitated a large number of proteins, many of which have been described in earlier studies[15] and were common to all three HP1 proteins. They also observed a number of proteins that interacted uniquely with specific isoforms, such as the previously identified CAF-1 or Senp7 interactions with HP1alpha[16,17]. In general, HP1beta and HP1gamma interactomes were more similar to each other than to that of HP1alpha. Intriguingly, both Adnp and Chd4 were highly enriched in HP1beta and HP1gamma purifications. In contrast, Chd4 did not co-purify with HP1alpha, and Adnp was 100-fold and 235-fold more abundant in HP1beta and HP1gamma purifications, respectively, as compared to HP1alpha purification. These results strongly support stable interactions between Adnp, HP1beta, HP1gamma and Chd4 in mES cells. Chd4 is a member of the nucleosome remodeling and deacetylase (NuRD) complex[18-20], which was recovered by LC-MS/MS analysis of single-step streptavidin purification of endogenously tagged Chd4. NuRD was not identified in Adnp purifications under the same conditions, indicating that Chd4 might be part of two distinct complexes. Indeed, separation of mES cell extracts by gel filtration revealed co-migration of Chd4 with NuRD components or HP1 and Adnp in different high-molecular weight complexes. This is consistent with Adnp forming a stable and distinct complex with Chd4 and HP1.

In Vitro Reconstitution of the ChAHP Complex

To test this directly, and to explore potential conservation, the inventors set out to reconstitute complex formation in vitro with recombinant human ADNP, HP1gamma, and CHD4 expressed in Hi5 insect cells. Co-lysis of cells expressing HP1gamma, Adnp, and Chd4 resulted in the formation of a trimeric complex, which was preserved after strep-affinity purification, anion-exchange and size exclusion chromatography (SEC). To dissect the individual interactions within the complex, they expressed recombinant full length or truncated variants of the proteins and performed pulldown experiments. This revealed that ADNP binds to both CHD4 and HP1gamma while CHD4 and HP1gamma do not interact directly. Notably, N-terminally truncated ADNP did not co-elute with CHD4 on SEC. This was confirmed by pull down experiments, which showed that ADNP lacking the first 228 amino acids was only able to bind to HP1gamma but no longer to CHD4. Thus, ADNP contacts CHD4 through its N-terminus. Given the conserved P*V*L consensus pentapeptide in the C-terminus of ADNP the inventors speculated that the C-terminal part of ADNP may directly interact with the chromo shadow domain (CSD) of HP1gamma in a similar manner as previously described for other P*V*L containing proteins[13]. Indeed, the HP1gamma CSD interacted as efficiently with ADNP as full length HP1gamma whereas the HP1gamma chromo domain (CD) did not bind to ADNP. It was concluded that Chd4, Adnp, and HP1gamma form a stable protein complex, which is referred to as ChAHP. Adnp is at the core of the complex and interacts with the CSD of HP1 via its C-terminal P*V*L motif and with Chd4 via its N-terminus.

REFERENCES

Du, M., Jones, J. R., Lanier, J., Keeling, K. M., Lindsey, J. R., Tousson, A., Bebok, Z., Whitsett, J. A., Dey, C. R., Colledge, W. H., Evans, M. J., Sorscher, E. J. and Bedwell, D. M. (2002) 'Aminoglycoside suppression of a premature stop mutation in a Cftr–/– mouse carrying a human CFTR-G542X transgene', *J Mol Med (Berl)*, 80(9), 595-604.

Helip-Wooley, A., Park, M. A., Lemons, R. M. and Thoene, J. G. (2002) 'Expression of CTNS alleles: subcellular localization and aminoglycoside correction in vitro', *Mol Genet Metab*, 75(2), 128-33.

Keeling, K. M., Brooks, D. A., Hopwood, J. J., Li, P., Thompson, J. N. and Bedwell, D. M. (2001) 'Gentamicin-mediated suppression of Hurler syndrome stop mutations restores a low level of alpha-L-iduronidase activity and reduces lysosomal glycosaminoglycan accumulation', *Hum Mol Genet*, 10(3), 291-9.

Lai, C. H., Chun, H. H., Nahas, S. A., Mitui, M., Gamo, K. M., Du, L. and Gatti, R. A. (2004) 'Correction of ATM gene function by aminoglycoside-induced read-through of premature termination codons', *Proc Natl Acad Sci USA*, 101(44), 15676-81.

Loufrani, L., Dubroca, C., You, D., Li, Z., Levy, B., Paulin, D. and Henrion, D. (2004) 'Absence of dystrophin in mice reduces NO-dependent vascular function and vascular density: total recovery after a treatment with the aminoglycoside gentamicin', *Arterioscler Thromb Vasc Biol*, 24(4), 671-6.

Rebibo-Sabbah, A., Nudelman, I., Ahmed, Z. M., Baasov, T. and Ben-Yosef, T. (2007) 'In vitro and ex vivo suppression by aminoglycosides of PCDH15 nonsense mutations underlying type 1 Usher syndrome', *Hum Genet*, 122(3-4), 373-81.

Sossi, V., Giuli, A., Vitali, T., Tiziano, F., Mirabella, M., Antonelli, A., Neri, G. and Brahe, C. (2001) 'Premature termination mutations in exon 3 of the SMN1 gene are associated with exon skipping and a relatively mild SMA phenotype', *Eur J Hum Genet*, 9(2), 113-20.

Zingman, L. V., Park, S., Olson, T. M., Alekseev, A. E. and Terzic, A. (2007) 'Aminoglycoside-induced translational read-through in disease: overcoming nonsense mutations by pharmacogenetic therapy', *Clin Pharmacol Ther*, 81(1), 99-103.

1. Bassan, M. et al. Complete sequence of a novel protein containing a femtomolar-activity-dependent neuroprotective peptide. *J. Neurochem.* 72, 1283-1293 (1999).
2. Zamostiano, R. et al. Cloning and characterization of the human activity-dependent neuroprotective protein. *Journal of Biological Chemistry* 276, 708-714 (2001).
3. Pinhasov, A. et al. Activity-dependent neuroprotective protein: a novel gene essential for brain formation. *Developmental Brain Research* 144, 83-90 (2003).
4. Mandel, S., Rechavi, G. & Gozes, I. Activity-dependent neuroprotective protein (ADNP) differentially interacts with chromatin to regulate genes essential for embryogenesis. *Dev. Biol.* 303, 814-824 (2007).
5. Helsmoortel, C. et al. A SWI/SNF-related autism syndrome caused by de novo mutations in ADNP. *Nature Publishing Group* 46, 380-384 (2014).
6. Niwa, H. Mouse ES cell culture system as a model of development. *Dev. Growth Differ.* 52, 275-283 (2010).
7. Flemr, M. & Bühler, M. Single-Step Generation of Conditional Knockout Mouse Embryonic Stem Cells. *Cell Rep* 12, 709-716 (2015).
8. Heinz, S. et al. Simple combinations of lineage-determining transcription factors prime cis-regulatory elements required for macrophage and B cell identities. *Mol. Cell* 38, 576-589 (2010).
9. Molkentin, J. D. The zinc finger-containing transcription factors GATA-4, -5, and -6. Ubiquitously expressed regulators of tissue-specific gene expression. *Journal of Biological Chemistry* 275, 38949-38952 (2000).
10. Fujikura, J. et al. Differentiation of embryonic stem cells is induced by GATA factors. *Genes Dev.* 16, 784-789 (2002).
11. Cho, L. T. Y. et al. Conversion from mouse embryonic to extra-embryonic endoderm stem cells reveals distinct differentiation capacities of pluripotent stem cell states. *Development* 139, 2866-2877 (2012).
12. Mosch, K., Franz, H., Soeroes, S., Singh, P. B. & Fischle, W. HP1 recruits activity-dependent neuroprotective protein to H3K9me3 marked pericentromeric heterochromatin for silencing of major satellite repeats. *PLoS ONE* 6, e15894 (2011).
13. Smothers, J. F. & Henikoff, S. The HP1 chromo shadow domain binds a consensus peptide pentamer. *Current Biology* 10, 27-30 (2000).
14. Mandel, S. & Gozes, I. Activity-dependent neuroprotective protein constitutes a novel element in the SWI/SNF chromatin remodeling complex. *Journal of Biological Chemistry* 282, 34448-34456 (2007).
15. Kwon, S. H. & Workman, J. L. The heterochromatin protein 1 (HP1) family: put away a bias toward HP1. *Mol. Cells* 26, 217-227 (2008).
16. Murzina, N., Verreault, A., Laue, E. & Stillman, B. Heterochromatin dynamics in mouse cells: interaction between chromatin assembly factor 1 and HP1 proteins. *Mol. Cell* 4, 529-540 (1999).
17. Maison, C. et al. The SUMO protease SENP7 is a critical component to ensure HP1 enrichment at pericentric heterochromatin. *Nat. Struct. Mol. Biol.* 19, 458-460 (2012).
18. Wade, P. A., Jones, P. L., Vermaak, D. & Wolffe, A. P. A multiple subunit Mi-2 histone deacetylase from *Xenopus laevis* cofractionates with an associated Snf2 superfamily ATPase. *Current Biology* 8, 843-846 (1998).

19. Xue, Y. et al. NURD, a novel complex with both ATP-dependent chromatin-remodeling and histone deacetylase activities. *Mol. Cell* 2, 851-861 (1998).
20. Zhang, Y., LeRoy, G., Seelig, H. P., Lane, W. S. & Reinberg, D. The dermatomyositis-specific autoantigen Mil is a component of a complex containing histone deacetylase and nucleosome remodeling activities. *Cell* 95, 279-289 (1998).
21. de Dieuleveult, M. et al. Genome-wide nucleosome specificity and function of chromatin remodellers in ES cells. *Nature* 530, 113-116 (2016).
22. O'Shaughnessy-Kirwan, A., Signolet, J., Costello, I., Gharbi, S. & Hendrich, B. Constraint of gene expression by the chromatin remodelling protein CHD4 facilitates lineage specification. *Development* 142, 2586-2597 (2015).
23. Bannister, A. J. et al. Selective recognition of methylated lysine 9 on histone H3 by the HP1 chromo domain. *Nature* 410, 120-124 (2001).
24. Lachner, M., O'Carroll, D., Rea, S., Mechtler, K. & Jenuwein, T. Methylation of histone H3 lysine 9 creates a binding site for HP1 proteins. *Nature* 410, 116-120 (2001).
25. Voss, T. C. & Hager, G. L. Dynamic regulation of transcriptional states by chromatin and transcription factors. *Nature Publishing Group* 15, 69-81 (2014).
26. Rosnoblet, C., Vandamme, J., Volkel, P. & Angrand, P.-O. Analysis of the human HP1 interactome reveals novel binding partners. *Biochem. Biophys. Res. Commun.* 413, 206-211 (2011).
27. Gozes, I., Yeheskel, A. & Pasmanik-Chor, M. Activity-dependent neuroprotective protein (ADNP): a case study for highly conserved chordata-specific genes shaping the brain and mutated in cancer. *J. Alzheimers Dis.* 45, 57-73 (2015).
28. Gozes, I. et al. The Compassionate Side of Neuroscience: Tony Sermone's Undiagnosed Genetic Journey—ADNP Mutation. *J Mol Neurosci* 56, 751-757 (2015).
29. Peltz, S. W., Morsy, M., Welch, E. M. & Jacobson, A. Ataluren as an agent for therapeutic nonsense suppression. *Annu. Rev. Med.* 64, 407-425 (2013).
30. Welch, E. M. et al. PTC124 targets genetic disorders caused by nonsense mutations. *Nature* 447, 87-91 (2007).
31. Vizcaíno, J. A. et al. 2016 update of the PRIDE database and its related tools. *Nucleic Acids Res.* 44, D447-56 (2016).
32. Mohn, F. et al. Lineage-specific polycomb targets and de novo DNA methylation define restriction and potential of neuronal progenitors. *Mol. Cell* 30, 755-766 (2008).
33. Cox, J. et al. Andromeda: a peptide search engine integrated into the MaxQuant environment. *J. Proteome Res.* 10, 1794-1805 (2011).
34. Cox, J. et al. Accurate proteome-wide label-free quantification by delayed normalization and maximal peptide ratio extraction, termed MaxLFQ. *Mol. Cell Proteomics* 13, 2513-2526 (2014).
35. Hubner, N. C. et al. Quantitative proteomics combined with BAC TransgeneOmics reveals in vivo protein interactions. *J. Cell Biol.* 189, 739-754 (2010).
36. Tyanova, S. et al. The Perseus computational platform for comprehensive analysis of (prote)omics data. *Nat Meth* 13, 731-740 (2016).
37. Tusher, V. G., Tibshirani, R. & Chu, G. Significance analysis of microarrays applied to the ionizing radiation response. *Proc. Natl. Acad. Sci. U.S.A.* 98, 5116-5121 (2001).
38. Schwanhäusser, B. et al. Global quantification of mammalian gene expression control. *Nature* 473, 337-342 (2011).
39. Rosenbloom, K. R. et al. The UCSC Genome Browser database: 2015 update. *Nucleic Acids Res.* 43, D670-81 (2015).
40. Langmead, B., Trapnell, C., Pop, M. & Salzberg, S. L. Ultrafast and memory-efficient alignment of short DNA sequences to the human genome. *Genome Biol* 10, R25 (2009).
41. Gaidatzis, D., Lerch, A., Hahne, F. & Stadler, M. B. QuasR: quantification and annotation of short reads in R. *Bioinformatics* 31, 1130-1132 (2015).
42. Robinson, M. D., McCarthy, D. J. & Smyth, G. K. edgeR: a Bioconductor package for differential expression analysis of digital gene expression data. *Bioinformatics* 26, 139-140 (2010).
43. Tripathi, S. et al. Meta- and Orthogonal Integration of Influenza 'OMICs' Data Defines a Role for UBR4 in Virus Budding. *Cell Host Microbe* 18, 723-735 (2015).
44. Zhang, Y. et al. Model-based analysis of ChIP-Seq (MACS). *Genome Biol* 9, R137 (2008).
45. Ramirez, F. et al. deepTools2: a next generation web server for deep-sequencing data analysis. *Nucleic Acids Res.* 44, W160-5 (2016).
46. Whyte, W. A. et al. Enhancer decommissioning by LSD1 during embryonic stem cell differentiation. *Nature* 482, 221-225 (2012).
47. Tiwari, V. K. et al. A chromatin-modifying function of JNK during stem cell differentiation. *Nat Genet* 44, 94-100 (2011).
48. Karmodiya, K., Krebs, A. R., Oulad-Abdelghani, M., Kimura, H. & Tora, L. H3K9 and H3K14 acetylation co-occur at many gene regulatory elements, while H3K14ac marks a subset of inactive inducible promoters in mouse embryonic stem cells. *BMC Genomics* 13, 424 (2012).
49. Liu, N. et al. Recognition of H3K9 methylation by GLP is required for efficient establishment of H3K9 methylation, rapid target gene repression, and mouse viability. *Genes Dev.* 29, 379-393 (2015).
50. Mikkelsen, T. S. et al. Genome-wide maps of chromatin state in pluripotent and lineage-committed cells. *Nature* 448, 553-560 (2007).
51. Abdulrahman, W. et al. A set of baculovirus transfer vectors for screening of affinity tags and parallel expression strategies. *Anal. Biochem.* 385, 383-385 (2009).

The invention claimed is:

1. A method of reducing a symptom or progression of Autism Spectrum Disorder (ASD), comprising administering a therapeutically effective amount of a pharmaceutical composition comprising a compound promoting ribosomal read-through of premature stop codons to a subject in need thereof, said compound being selected from the group consisting of gentamicin, streptomycin, amikacin, kanamycin, tobramycin, netilmicin, neomycin, framycetin, negamycin, paromomycin, hygromycin B, apramycin, dihydrostreptomycin, sisomicin, erythromycin, NPC-14 (arbekacin), ELX-02, G-418, ribostamycin, bekanamycin, dibekacin, spectinomycin, chloramphenicol, azidamfenicol, thiamphenicol, florfenicol, linezolid, eperzolid, posizolid, radezolid, ranbezolid, sutezolid, tedizolid, PTC 124 (ataluren), RTC 13, RTC 14, amlexanox, tylosin, and structural derivatives or structural analogs thereof, wherein the Autism Spectrum Disorder (ASD) is selected from the group consisting of Helsmoortel-van der Aa syndrome and Sifrim-Hitz-Weiss syndrome.

2. The method according to claim 1, wherein the compound is selected from the group consisting of chloramphenicol, azidamfenicol, thiamphenicol, florfenicol and structural derivatives or structural analogs thereof.

3. The method according to claim 1, wherein the compound is selected from the group consisting of linezolid, eperzolid, posizolid, radezolid, ranbezolid, sutezolid, tedizolid and structural analogs or structural derivatives thereof.

4. The method according to claim 1, wherein the compound is selected from the group consisting of PTC 124 (ataluren), RTC 13, RTC 14, amlexanox and tylosin.

5. The method according to claim 1, wherein the Autism Spectrum Disorder (ASD) is characterized by at least one non-sense mutation in gene ADNP.

6. The method according to claim 5, wherein the non-sense mutation in the ADNP gene is selected from the group consisting of c.1046_1047delTG, c.118C>T, c.1211C>A, c.1222_1223delAA, c.1222_1224delAAGinsG, c.1553G>A, c.1668G>C, c.1930C>T, c.2153_2165delCTTACGAGCAAAT, c.2156_2157insA, c.2157C>G, c.2157del, c.2157delCinsAC, c.2188C>T, c.2213C>G, c.2288C>T, c.2318_2319del, c.2490_2494delATTAAinsA, c.2491_2494delTTAA, c.2491_2499delTTAAATAAAinsTTAAA, c.2495_2499delATAAAinsA, c.2496_2499delTAAA, c.2866_2869del, c.2881G>T, c.3047dup, c.3066_3072delCAGAGAGinsCAG, c.3170T>A, c.3280_3281insCC, c.3281G>T, c.632T>A, c.642_649del, c.673C>T, delTGAC, and c.2495_2500delATAAAGinsAG.

7. The method according to claim 1, wherein the Autism Spectrum Disorder (ASD) is Helsmoortel-van der Aa syndrome.

8. The method according to claim 1, wherein the Autism Spectrum Disorder (ASD) is Sifrim-Hitz-Weiss syndrome.

9. The method according to claim 1, wherein compound is selected from the group consisting of gentamicin, streptomycin, amikacin, kanamycin, tobramycin, netilmicin, neomycin, framycetin, negamycin, paromomycin, hygromycin B, apramycin, dihydrostreptomycin, sisomicin, erythromycin, NPC-14 (arbekacin), ELX-02, G-418, ribostamycin, bekanamycin, dibekacin, spectinomycin and structural derivatives or structural analogs thereof.

* * * * *